United States Patent [19]
Walkowiak et al.

[11] Patent Number: 4,707,504
[45] Date of Patent: Nov. 17, 1987

[54] POROUS FILLERS IN POLYMERIZABLE COMPOSITIONS

[75] Inventors: Michael Walkowiak; Klaus Nehren, both of Leverkusen; Wolfgang Podszun, Cologne; Werner Finger, Leverkusen, all of Fed. Rep. of Germany

[73] Assignee: Bayer Aktiengesellschaft, Leverkusen, Fed. Rep. of Germany

[21] Appl. No.: 762,987

[22] Filed: Aug. 6, 1985

[30] Foreign Application Priority Data

Aug. 22, 1984 [DE] Fed. Rep. of Germany ....... 3430801

[51] Int. Cl.$^4$ .......................... C08F 2/44; C08K 9/06; C08K 3/36; A61K 5/06
[52] U.S. Cl. .................................... 523/109; 523/113; 523/115; 523/116; 523/212; 523/216; 523/218; 523/219; 523/220; 524/786; 524/791; 524/854
[58] Field of Search ............... 523/212, 218, 219, 220, 523/116, 216, , 113, 115, 109; 524/786, 791, 854

[56] References Cited

U.S. PATENT DOCUMENTS

| 4,431,568 | 2/1984 | Miya et al. | 526/124 |
| 4,452,951 | 6/1984 | Kubo et al. | 525/339 |
| 4,526,941 | 7/1985 | Sakurai et al. | 526/129 |
| 4,552,906 | 11/1985 | Podszun et al. | 523/116 |

Primary Examiner—Herbert J. Lilling
Attorney, Agent, or Firm—Sprung Horn Kramer & Woods

[57] ABSTRACT

The use of microporous inorganic fillers in polymerizable compositions, in particular in the dental field, characterized in that the fillers have (a) an average particle size of 0.5 to 50μ,
(b) a BET-surface area of at least 200 m$^2$/g,
(c) a pore volume of 0.7 to 5 ml/g and
(d) a pore diameter of 10 to 50 nm.

Fillings made therefrom are smooth and easy to polish.

17 Claims, No Drawings

POROUS FILLERS IN POLYMERIZABLE COMPOSITIONS

The present invention relates to the use of porous inorganic particles defined in more detail below, in particular of $SiO_2$ or silicates, as fillers for polymerizable compositions, preferably dental compositions. The compositions according to the invention can be used, for example, for dental restoration and repair work, as crown and bridge materials and for the production of false teeth.

Hardenable filler-containing dental compositions based on ethylenically unsaturated polymerizable monomers (in particular mono-, di- and poly-functional esters of acrylic and methacrylic acid) are known, for example, from U.S. Pat. Nos. 3,066,112, 3,926,906 and British Patent Specification No. 1,544,776. The (inorganic) fillers must be added to the polymerizable compositions to reduce their polymerization shrinkage, to lower the coefficient of thermal expansion and to increase the hardness of the polymers obtained.

The amount of inert inorganic fillers in such dental materials can be up to over 80% of the total composition. Examples of fillers used are quartz, quartz glass or silicate glasses, such as lithium aluminum silicate or barium silicate glass, as fine powders. The particle sizes of these fillers are in the range from 1 to about 100 $\mu$m, the average particle diameter in general being of the order of about 10 $\mu$m.

The disadvantage in using these known fillers is that the dental materials produced therefrom are not yet satisfactorily abrasion-resistant and have a surface roughness when used as dental fillings. As a result of their poor abrasion properties, it has not been possible to use the dental filling materials containing such fillers in the region of posterior teeth, so that at present the amalgam fillings still prevail there.

However, the surface roughness of the materials mentioned also leads to problems when these are used in the region of anterior teeth, since deposition of dental plaque is promoted here and both discoloration and marginal secondary caries can thereby be caused.

In order to eliminate the disadvantages of surface roughness, German Patent Specification No. 2,403,211 proposes the use, as a filler, of highly disperse silicon dioxide obtained by flame pyrolysis, the particle size of which should be in the range from 10 to 400 nm; the BET surface area should be less than 200 $m^2/g$; the unsuitability of precipitated silicic acids is expressly referred to.

A combination of macrofiller and microfiller composites is described in European Patent Application No. 0,060,911. According to European Patent Application No. 0,040,232, granulation of pyrogenic or precipitated silicon dioxide with waterglass or boric acid gives stable agglomerates which allow higher degrees of filling and can be polished. The use of microporous fillers is also known per se. Porous glasses are described, for example, in U.S. Pat. Nos. 2,106,744, 3,549,524 and 4,306,913. Porous fillers can also be obtained by sintering glass fibers, as described in European Patent Application No. 0,048,681. These conventional microporous fillers have a specific surface area of not more than about 20 $m^2/g$.

A decisive weak point of the macrofillers hitherto known is the poor bonding between the filler surface and polymer matrix, which can be only partly improved by surface treatment. Although the bonding can be increased by increasing the surface area or the number of pores, fractographs obtained by scanning electron microscopy then also show, as is the case with the agglomerates, inadequate bonding between the filler surface and polymer matrix. A summary of the advantages and disadvantages of the individual systems in respect of their clinical properties is given by Lutz, Phillips, Roulet and Imfeld in Schweiz. Mschr. Zahnheilkunde 93, 914-929 (1983).

It has now been found, surprisingly, that synthetic amorphous highly porous particles which are known per se, in particular silicic acids, such as are described as matting agents in, for example, DE-OS (German Published Specification) No. 2,145,090 (U.S. Pat. No. 3,959,174), DE-OS (German Published Specification) Nos. 2,124,223 and 2,853,647, exhibit outstanding properties as fillers.

The invention relates to the use of microporous inorganic fillers in polymerizable compositions, characterized in that the fillers have (a) an average particle size of 0.5-50 $\mu$, preferably 1-20 $\mu$; (b) a BET surface area of at least 200 $m^2/g$, preferably 300-600 $m^2/g$; (c) a pore volume of 0.7-5 ml/g, preferably 1-3 ml/g; and (d) a pore diameter of 10-50 nm, preferably about 20 nm.

The invention furthermore relates to polymerizable compositions, in particular dental compositions, containing 20 to 65% by weight, preferably 30 to 60% by weight, of a polymerizable monomer and 10 to 60%, preferably 30 to 50% by weight, of an inorganic filler and, if appropriate, additives which are known per se, characterized in that the filler fulfils the abovementioned criteria.

Finally, the invention also relates to a process for the production of shaped articles, in particular dental shaped articles, characterized in that a composition according to the invention is polymerized, while being shaped.

Although the microporous fillers to be used according to the invention have a relatively large average particle diameter, the shaped articles produced according to the invention (in particular dental fillings) are outstandingly easy to polish. Pictures of fracture surfaces obtained by scanning electron microscopy show a smooth surface such as is otherwise only known of materials which are built up homogeneously.

Surprisingly, the shaped articles produced according to the invention are also substantially transparent, although the refractive indices of, for example, amorphous silicic acid (1.46) and conventional, polymerized methacrylic acid esters, such as bis-GMA/triethylene glycol dimethacrylate (1.55) differ noticeably. In contrast to the prejudice expressed in DE-OS (German Published Specification) No. 2,403,211, precisely those fillers with a BET surface area greater than 200 $m^2/g$ (preferably 300-600 $m^2/g$) show the best properties.

The microporous fillers to be used according to the invention are commercially available (for example Syloid ® grades from W. R. Grace & Co., New York). They can be prepared, for example, by the processes described in DE-OS (German Published Specification) Nos. 2,145,090 and 2,853,647. Possible starting materials here are in principle all the gel-forming inorganic oxides and salts, in particular $SiO_2$, $Al_2O_3$ and silicates (preferably Ca silicates).

If appropriate, before being used according to the invention, the fillers can be surface-treated in a manner which is known per se. Organosilicon compounds in an amount of 5-40% by weight, based on the filler, are preferably employed for this purpose. Examples of suitable compounds are vinyltriethoxysilane, vinyltrichlorosilane, vinyltrimethoxysilane, allyldimethylchlorosilane, γ-methacryloxypropyltrimethoxysilane, β-(3,4-epoxycyclohexyl-ethyltrimethoxysilane and γ-glycidoxy-propyltrimethoxysilane, and also disilazanes, such as hexamethyldisilazane or vinyldisilazanes.

The fillers to be used according to the invention can be employed by themselves or together with other fillers, preferably microfine fillers (particle size <500 nm), which are known per se, and which can optionally also be silanized or grafted with (meth)acrylates. These fillers can be added in amounts of, for example, 1-40% by weight, preferably 5-20% by weight, based on the polymerizable composition.

The monomers to be used in the compositions according to the invention contain at least one double bond which can undergo free radical polymerization. Monomers with more than one double bond and with boiling points above 100° C. at 13 mbar are preferably used, by themselves or, if appropriate, mixed with monofunctional monomers. Highly crosslinked polymers or copolymers are thereby obtained. The molecular weights of the monomers can be between about 70 and 20,000, preferably between about 150 and 1,000. The viscosity of the monomers can be adjusted by suitable mixing of monomers of higher viscosity or higher molecular weight with low-viscosity monomers. If appropriate, the monomers contain small amounts of polymerization inhibitors, such as, for example, 0.01-0.2% of 2,6-di-t-butyl-p-cresol.

Examples of possible polymerizable monomers to be used according to the invention are: esters of unsaturated mono- or di-carboxylic acids, for example esters of acrylic, methacrylic, α-cyanoacrylic, crotonic, cinnamic, sorbic, maleic, fumaric or itaconic acid with aliphatic, cycloaliphatic or aromatic-aliphatic mono-, di-, tri- or tetra-hydric alcohols with 2-30 carbon atoms, for example methyl (meth)acrylate, n-, i- or t-butyl (meth)acrylate, 2-ethylhexyl (meth)acrylate, lauryl (meth)acrylate, dihydrodicyclopentadienyl (meth)acrylate, di-hydroxymethyl-tricyclo [5,2,1,0,2,6]decane di(meth) acrylate according to German Patent Specification No. 2,200,021, methylglycol di(meth)acrylate, hydroxyethyl (meth)acrylate, hydroxypropyl (meth)acrylate, ethylene glycol di(meth)acrylate, diethylene glycol di(meth)acrylate, triethylene glycol di(meth)acrylate, neopentylglycol di(meth)acrylate, 1,4-dimethylolcyclohexane di-(meth)acrylate, pentaerythritol tri- and tetra-(meth)acrylate, trimethylolpropane tri(-meth)acrylate, ethylα-cyanoacrylate, ethyl crotonate, ethyl sorbate, diethyl maleate, diethyl fumarate and the di(meth)acrylate of oxyalkylated bisphenol A according to U.S. Pat. Nos. 3,810,938 and 3,923,740, di(meth)acrylic acid esters of oxyalkylated trimethylolpropane or pentaerythritol according to U.S. Pat. No. 3,380,831, and also the (meth)acrylic acid esters of oxyalkylated di-(hydroxymethyl)tricyclo)[5,2,1,0,2,6]-decanes, such as are described in DE-OS (German Published Specification) Nos. 2,931,925 and 2,931,926.

Other monomers which can be employed in the compositions according to the invention are amides of (meth)acrylic acid, which can optionally be substituted on the nitrogen atom by alkyl, alkoxyalkyl or hydroxyalkyl radicals, such as, for example, N-isobutylacrylamide, diacetoneacrylamide, N-methylolacrylamide, N-methoxymethylacrylamide, N-butoxymethylmethacrylamide, ethylene glycol bis-(N-methylolacrylamide) ether and methylene-bis-acrylamide; triacrylformal; vinyl esters of mono- and di-carboxylic acids with 2 to 20 carbon atoms, for example vinyl acetate, vinyl propionate, vinyl 2-ethylhexanoate, vinyl versatate and divinyl adipate; vinyl ethers of monohydric or dihydric alcohols with 3 to 20 carbon atoms, for example isobutyl vinyl ether, octadecyl vinyl ether, ethylene glycol divinyl ether and diethylene glycol divinyl ether; mono-N-vinyl compounds, for example N-vinylpyrrolidone, N-vinylpiperidone, N-vinylcaprolactam, N-vinylmorpholine, N-vinyloxazolidone, N-vinylsuccinimide, N-methyl-N-vinylformamide and N-vinylcarbazole; allyl ethers and esters, for example trimethylolpropane diallyl ether, trimethylolpropane triallyl ether, allyl (meth)acrylate, diallyl maleate, diallyl phthalate and prepolymers thereof, and any desired mixtures of all the unsaturated compounds mentioned.

The epoxide acrylates and urethane acrylates are particularly suitable for medical purposes. Examples of such compounds which may be mentioned are: (a) reaction products of monofunctional epoxides and (meth)acrylic acid according to U.S. Pat. Nos. 2,484,487 and 2,575,440; (b) reaction products of bifunctional epoxides and unsaturated fatty acids according to U.S. Pat. No. 2,456,408; (c) reaction products of polyfunctional aromatic or aliphatic glycidyl ethers and (meth)acrylic acid according to U.S. Pat. Nos. 3,179,623, 3,066,112 and 2,824,851 and German Patent Specification No. 1,644,817; (d) reaction products of epoxy resins and (meth)acryloyl chloride according to U.S. Pat. Nos. 3,427,161 and 2,890,202; and (e) unsaturated polyurethanes (urethane acrylates) and polyureas of hydroxyalkyl (meth)acrylates, aminoalkyl (meth)acrylates and, if appropriate, polyols or polyamines, such as are described in U.S. Pat. Nos. 3,425,988, 3,709,866, 3,629,187, 4,089,763 and 4,110,184, and German Patent Specification Nos. 1,644,798 and 1,644,797 and DOS (Germar Published Specification) Nos. 2,357,402, 2,357,324 and 2,358,948.

Other examples of suitable comonomers can be seen from the summary below; in the structural formulae, R represents

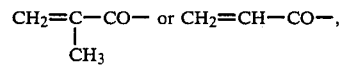

R' represents H or $CH_2$—OR
n represents a number between 1 and 4 and
m represents a number between 0 and 4

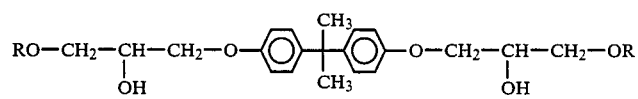

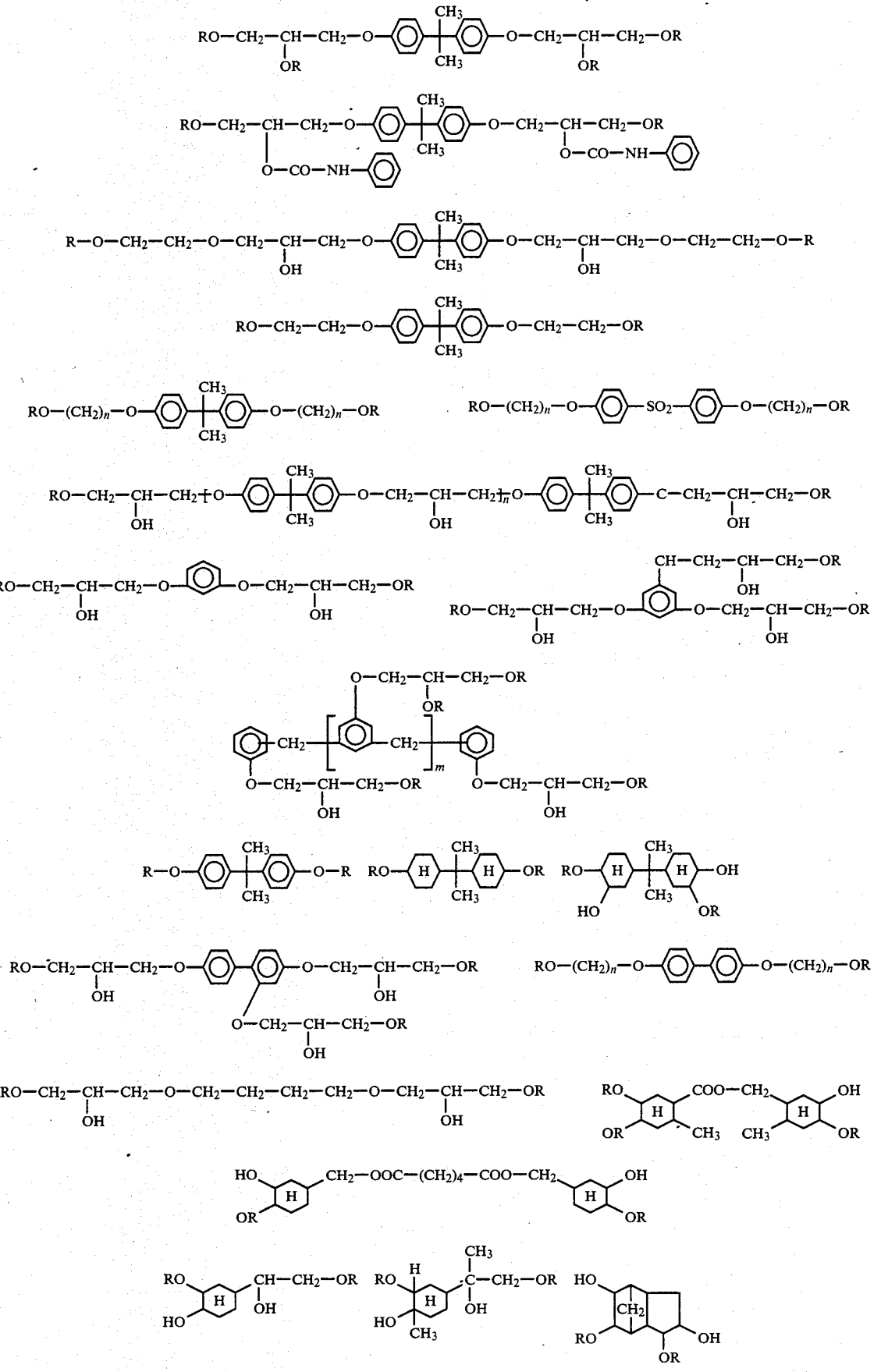

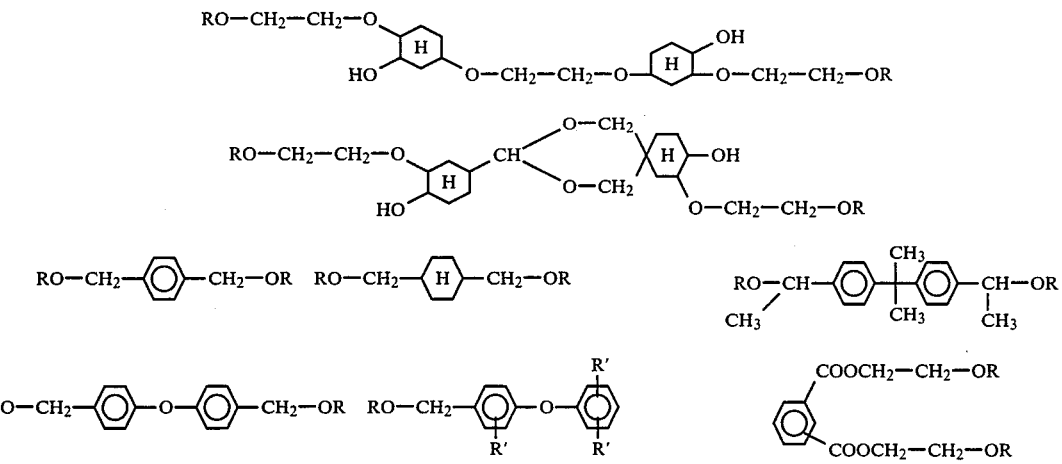

in the ortho-, meta- or para-form

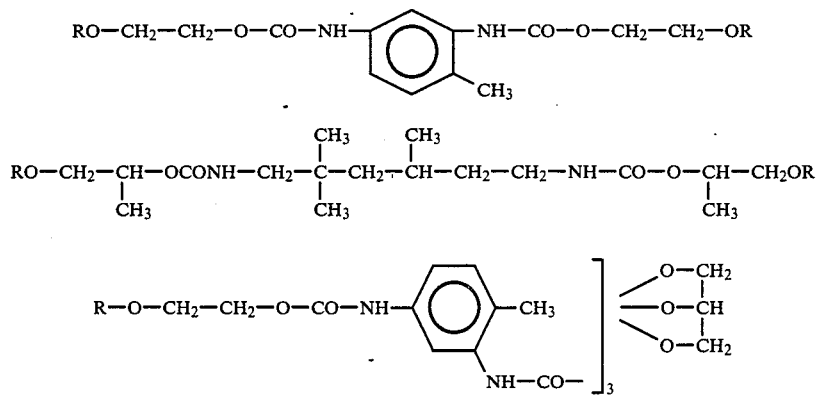

and compounds of the general formula

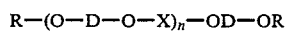

wherein
HO—D—OH represents a polyol and
HO—X—OH represents a dicarboxylic acid, each of which can be saturated or unsaturated and cyclic or acyclic.

Depending on the intended use, it is also possible additionally to use other substances in the compositions according to the invention, such as, for example, other inorganic and/or organic fillers and pigments, stabilizers, dyestuffs, particular light stabilisers, fluorescence agents, plasticisers and soluble, swellable or insoluble high molecular weight compounds.

Pastes which are particularly suitable as a dental material are obtained if at least portions of compounds of the bis-GMA type of the formula

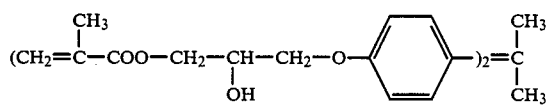

are employed as the esters of methacrylic acid.

Dental filling compositions with a good consistency and a high level of mechanical strength are obtained in particular if mixtures of various methacrylic acid esters are used as the esters of methacrylic acid, for example mixtures of 20–70 parts by weight of bis-GMA and 30–80 parts by weight of triethylene glycol dimethacrylate (TEGDMA).

Starter additives which can be used for initiating the polymerisation are the customary starter systems, that is to say systems which supply free radicals, anions or cations and which can trigger off free radical, anionic or cationic polymerisation. In the case of systems which supply free radicals, peroxides or aliphatic azo compounds are particularly suitable, for example benzoyl peroxide, lauryl peroxide or azoisobutyrodinitrile, which are usually employed in amounts of 0.1 to 5% by weight. Whilst hardening at elevated temperature can be carried out by peroxides or other free radical starters alone, it is in general necessary to add accelerators, preferably aromatic amines, for hardening at room temperature. Examples of suitable accelerators are N,N-substituted toluidines and xylidines, such as N,N-dimethyl-p-toluidine or N,N-bis(2-hydroxy-ethyl)xylidine. Good hardening times are achieved by adding 0.5–3% of amine. An advantageous presentation form for a system activated with peroxide and accelerator is the 2-paste form, in which one paste contains the free radical starter and the other the accelerator and hardening is initiated by mixing the two pastes.

However, it is also possible to prepare one-phase products which polymerize under the action of light, for example UV light, visible light or a laser beam, and then of course contain a photopolymerization initiator and, if appropriate, also an accelerator for this purpose.

Appropriate photopolymerization initiators are known, and these are preferably carbonyl compounds, such as benzoin and derivatives thereof, in particular benzoin methyl ether, benzil and benzil derivatives, for example 4,4-oxydibenzil or other dicarbonyl compounds, for example diacetyl, 2,3-pentanedione or metal carbonyls, and quinones or derivatives thereof. The amount of such photopolymerisation initiators is preferably about 0.01 to about 5% by weight of the total composition.

These photohardenable, that is to say photopolymerizable, products preferably also additionally contain substances which accelerate the polymerization reaction in the presence of photopolymerization initiators. Examples of known accelerators are aromatic amines, such as p-toluidine and dimethyl-p-toluidine, trialkylamines, such as trihexylamine, polyamines, such as N,N,N',N'-tetraalkylalkylenediamines, barbituric acid and dialkylbarbituric acids, and sulphimides, preferably in an amount of about 0.01 to about 5% by weight of the total composition.

Finally, it is advantageous to add UV stabilizers to dental filling materials based on plastics, in order to avoid subsequent darkening during ageing of the fillings.

A particularly suitable UV stabilizer is 2- hydroxy-4-methoxybenzophenone. Another preferred material is 2-(2'-hydroxy-5'-methylphenyl)-benzotriazole; however, in principle any physiologically inert UV-absorbing agent is suitable for this purpose. Further examples which may be mentioned are thus hydroquinone, p-benzoquinone, p-butylhydroxytoluene and the like. The latter compound can also act, for example, as an antioxidant in the filling.

A review of the substances usually employed in dental filling materials is to be found in the article by R. L. Bowen in Journal of Dental Research, Volume 58/5 (May 1979), pages 1493 to 1503, and in the subsequent supplement by J. F. Lann, pages 1504 to 1506, as well as the literature references quoted therein.

To establish an impression of the filled dental surfaces which looks as natural as possible, composite materials necessarily also contain a small amount of dyestuffs or pigments.

If large amounts of polyfunctional monomers (crosslinking agents) are used and for particular intended uses, it may be advantageous to add plasticizers to the polymerizable compositions according to the invention in order to reduce the brittleness. Plasticizers which are particularly suitable are, above all, high molecular weight plasticizers which are known per se, in particular those based on polyurethanes, polycarbonates, polyesters and polyethers. Polyesters and polyester-carbonates, which are described in DE-OS (German Published Specification) No. 3,316,851, are preferred.

The compositions according to the invention are employed, in particular, for the preparation of polymers which come into contact with the human or animal body, for example as bone cements, dental materials and medical sealing compositions. In connection with dental materials, dental restoration compositions (in particular also dental filling compositions), crowns, bridges, veneers and similar dental prostheses and also artificial teeth may be mentioned in particular.

Preparation of the highly porous fillers to be used according to the invention:

1,072 g of sodium silicate solution,
172 g of ammonium hydroxide solution (29% strength) and,
1,756 g of water were mixed so that a total of 3,000 g of solution were obtained. The solution contained 300 g of silicic acid and 50 g of ammonia, corresponding to a silicon dioxide concentration of 10% and an $SiO_2:NH_2$ ratio of 6. Carbon dioxide was introduced into this solution, whereupon the pH value dropped to 10.91. The solution gelled within 4-6 minutes. This silicic acid hydrogel was aged for 10 minutes without stirring and for 50 minutes with stirring. Carbon dioxide was added for about one hour, until the pH value reached 9.0.

Sulphuric acid was then added in order to neutralize the sodium carbonate formed in the sodium silicate solution.

The solution was then aged at 60° C. for 16 hours. The product was dried and had the following properties:

| | |
|---|---|
| Total content of volatile constituents at 954° C. | 7% |
| $Na_2O$ (dry basis) | 0.03% |
| $SO_4$ (dry basis) | 0.02% |
| surface area (BET) | 400 $m^2/g$ |
| pore volume | 2.4 $cm^3/g$ |
| pore diameter about | 20 nm |

The dried silicic acid was fed into a 10 cm jet pulverizer mill using air with an inlet temperature of 427° C. under a pressure of 9.84 atmospheres gauge. The injection pressure for the silicic acid was 10.5 atmospheres gauge. The silicic acid discharged was collected in a sack collector. The silicic acid formed had an average particle size of 7 μm.

The pore volume of the filler can be adjusted in a controlled manner by varying the silicate concentration and the silicate/ammonia ratio as described in DE-OS (German Published Specification) No. 2,145,090. The particle size can be varied by suitably changing the grinding conditions.

EXAMPLE 1

A solution is prepared from:
31.0 g of bis-GMA (Bis-phenol-A diglycidyl dimethacrylate)
19.0 g of TEGDMA (triethyleneglyol dimethacrylate
0.25 g of N,N-dialkyl-p-dimethylaminobenzenesulphonamide
0.1 g of camphorquinone
0.06 g of benzil dimethyl ketal and
0.05 g of ionol.

26.0 g of a silicic acid silanized with 15.5% by weight of γ-methacryloxypropyltrimethoxysilane and with the following characteristic figures:

| | |
|---|---|
| average particle size: | 5μ |
| BET surface area: | 400 $m^2/g$ |
| pore volume: | 1.8 ml/g |
| pore diameter: | about 20 nm, | are added to 40 g of the above solution and the mixture is kneaded to a homogeneous composition.

After hardening of the composition with visible light, highly transparent test pieces with a flexural strength (according to DIN 13 992) of 83.06 N/mm$^2$, a flexural modulus of 3,310 N/mm$^2$ and a diametral tensile strength (according to ADA 27) of 35.6 N/mm$^2$ are obtained.

EXAMPLE 2

39.2 of TEGDMA are added to
80 g of the silicic acid from Example 1 and
16.8 g of pyrogenic silicic acid with a BET surface area of 50 m$^2$/g and a primary particle size of 45 nm in vacuo.
20.8 g of bis-GMA
0.15 g of the sulphonamide from Example 1
0.06 g of camphorquinone and
0.04 g of benzil dimethyl ketal
are added to 34.6 g of this mixture and the components are processed to a paste.

After hardening of the paste with visible light, transparent test pieces with the following mechanical properties are obtained:

| | |
|---|---|
| flexural strength: | 81.4 N/mm$^2$ |
| flexural modulus: | 3,738 N/mm$^2$ |
| diametral tensile strength: | 33 N/mm$^2$. |

EXAMPLE 3

(Comparison)

A solution is prepared from:
67.2 g of bis-GMA
41.2 g of TEGDMA
1.1 g of Tinuvin P
0.04 g of ionol
0.54 g of the sulphonamide from Example 1
0.14 g of benzil dimethyl ketal and
0.22 g of camphorquinone.
85.0 g of a silicic acid silanized with 9.3% by weight of γ-methacryloxypropyltrimethoxysilane (Syloid ®Al 1 from Grace) with the following characteristic data:

| | |
|---|---|
| pore volume: | 0.4 ml/g |
| average particle size: | 8μ |
| BET surface area: | 750 m$^2$/g |
| pore diameter | 4 nm | are added to 62.0 g of the above solution.
An opaque paste is obtained.

| | |
|---|---|
| Polymerization depth (Translux lamp) after exposure for seconds: | 5.0 mm |
| flexural strength: | 33.7 N/mm$^2$ |
| flexural modulus: | 4.186 N/mm$^2$ |
| diametral tensile strength: | 22.9 N/mm$^2$. |

The paste can easily be polished, but cannot be used as a dental filling material because of its high opacity.

EXAMPLE 4

100 g of the activated solution from Example 3 are processed to a paste with 51 g of a silicic acid which is silanized with 12% by weight of γ-methacryloxypropyltrimethoxysilane and has the following characteristic data:

| | |
|---|---|
| pore volume: | 1.6 ml/g |
| average particle diameter: | 2μ |
| BET surface area: | 400 m$^2$/g |
| pore diameter: | about 18 nm. |

After hardening with light, transparent test pieces which can very easily be polished are obtained.

| | |
|---|---|
| Polymerization depth (Translux) after 30 seconds: | 12 mm |
| flexural strength: | 76.6 N/mm$^2$ |
| flexural modulus: | 3,697 N/mm$^2$ |
| diametral tensile strength: | 37.7 N/mm$^2$. |

EXAMPLE 5

120 g of the activated solution from Example 3 are processed to a paste with 66 g of a silicic acid which is silanized with 18% by weight of γ-methacryloxypropyltrimethoxysilane and has the following characteristic data:

| | |
|---|---|
| pore volume: | 1.2 ml/g |
| average particle size: | 12μ |
| BET surface area: | 400 m$^2$/g |
| pore diameter: | about 13 nm. |

After hardening with light, adequately transparent test pieces which can very easily be polished are obtained.

| | |
|---|---|
| Polymerization depth (Transflux) | |
| after 30 seconds: | 8.8 mm |
| after 60 seconds: | 11 mm |
| flexural strength: | 69.3 N/mm$^2$ |
| flexural modulus: | 4,020 N/mm$^2$ |
| diametral tensile strength: | 37 N/mm$^2$. |

EXAMPLE 6

(A)

0.2 g of benzoyl peroxide and
5.4 g of a silicic acid treated with hexamethyldisilazane (containing 10.5% by weight of trimethylsilyl groups)
are added to a mixture of:
5.5 g of bis-GMA
2.3 g of TEGDMA and 2.0 g pf trimethylolpropane trimethacrylate:

| | |
|---|---|
| pore diameter: | about 20 nm |
| pore volume: | 1.8 ml/g |
| average particle diameter: | 5μ |
| BET surface area: | 500 m$^2$/g, | and the mixture is processed to paste.

(B)

0.09 of N-methyl-N-β-methylcarbamoyloxypropyl)-3,5-dimethylaniline and
5.5 g of the silicic acid described under (A) are added to 9.91 g of monomer mixture of the same composition as under (A) and the mixture is processed to a second paste.

Mixing pastes (A) and (B) in weight ratio 1:1 gives test pieces with the following physical properties:

| flexural strength: | 58.2 N/mm² |
|---|---|
| flexural modulus: | 3,450 N/mm² |
| diametral tensile strength: | 30.5 N/mm². |

EXAMPLE 7

(A)

0.2 g of benzoyl peroxide and
4.5 g of the silicic acid described in Example 6 (A) are added to a monomer mixture of
5.3 g of bis-GMA
3.5 g of TEGDMA and
1.0 g of pentaerythrol tetramethacrylate
and the mixture is processed to a paste.

(B) 0.7 g of N,N-dimethyltoluidine and 4.6 g of the silicic acid from Example 6 (A) are added to 9.9 g of monomer mixture as in (A), and the mixture is processed to a second paste.

Mixing pastes (A) and (B) in a ratio of 1:1 gives test pieces with the following physical properties:

| flexural strength: | 52.8 N/mm² |
|---|---|
| flexural modulus: | 3,517 N/mm² |
| diametral tensile strength: | 32.3 N/mm². |

EXAMPLE 8

(A)

A paste is prepared from
9.8 g of the methacrylic ester of oxyalkylated bis-hydroxymethyl-tricyclo[5.2.1.0.$^{2,6}$]decane (corresponding to European Patent No. 0,023,685, Example 1)
0.2 g of benzoyl peroxide and
4.8 g of the silicic acid described in Example 4.

(B) A second paste is prepared from
9.1 g of the above monomer,
0.9 g of bis-($\beta$-hydroxyethyl)-xylidine and
4.9 g of the silicic acid described in Example 4.

After mixing pastes (A) and (B) in a ratio of 1:1, test pieces with the following physical properties are obtained:

| flexural strength: | 62.6 N/mm² |
|---|---|
| flexural modulus: | 3,345 N/mm² |
| diametral tensile strength: | 38.2 N/mm². |

EXAMPLE 9

(A) A paste is prepared from
6.9 g of bis-GMA
2.9 g of TEGDMA
0.2 g of benzoyl peroxide and
5.0 g of the silicic acid described in Example 4.

(B)

A second paste is prepared from
6.9 g of bis-GMA
2.9 g of TEGDMA
0.09 g of N-methyl-N-$\beta$-(methylcarbamoyloxypropyl)-3,5-dimethylaniline and
5.0 g of the silicic acid described in Example 4.

After mixing pastes (A) and (B) in a ratio of 1:1, test pieces with the following physical properties are obtained:

| flexural strength: | 95.9 N/mm² |
|---|---|
| flexural modulus: | 3,364 N/mm² |
| diametral tensile strength: | 37.1 N/mm². |

It will be understood that the specification and examples are illustrative but not limitative of the present invention and that other embodiments within the spirit and scope of the invention will suggest themselves to those skilled in the art.

What is claimed is:

1. In a polymerizable composition containing a polymerizable monomer and a microporous inorganic filler, the improvement which comprises employing as the filler one which has
   (a) an average particle size of 0.5 to 50$\mu$;
   (b) a BET surface area of at least 200 m²/g;
   (c) a pore volume of 0.7 to 5 ml/g, and
   (d) a pore diameter of 10 to 50 nm.
2. A composition according to claim 1, wherein the composition is suitable for molding a dental material.
3. A composition according to claim 1, wherein the composition is suitable for molding a dental filling.
4. A composition according to claim 1, wherein the filler is silanized.
5. A composition according to claim 1, wherein the filler is at least one member selected from the group consisting of $SiO_2$, $Al_2O_3$ and calcium silicate.
6. A composition according to claim 1, wherein the filler comprises $SiO_2$.
7. A composition according to claim 1, additionally containing about 1 to 40% by weight of a finely disperse inorganic filler having a particle size below 500 nm.
8. A composition according to claim 1, wherein the polymerizable monomer comprises a mixture of monofunctional and polyfunctional methacrylic acid esters.
9. A composition according to claim 1, wherein the polymerizable monomer comprises bis-GMA.
10. A composition according to claim 1, wherein the polymerizable monomer is one which is polymerized by light or by a free radical-forming agent.
11. A composition according to claim 1, wherein the filler has
    (a) an average particle size of 1 to 20$\mu$;
    (b) a BET surface area of 300 to 600 m²/g;
    (c) a pore volume of 1 to 3 ml/g; and
    (d) a pore diameter of about 20 nm.
12. A composition according to claim 1, wherein the composition comprises by weight at least 20% of polymerizable monomer and at least 10% of the inorganic filler, any balance being made up of conventional additives.
13. A composition according to claim 12, wherein the composition by weight comprises 20 to 65% of polymerizable monomer and 10 to 60% of the inorganic filler.
14. A composition according to claim 12, wherein the composition by weight comprises 30 to 60% of polymerizable monomer and 30 to 50% of the inorganic filler.

15. A composition according to claim 11, wherein the filler comprises silanized $SiO_2$, the polymerizable monomer comprises bis-GMA, and the composition by weight comprises 30 to 60% of the polymerizable monomer, 30 to 50% of the inorganic filler and up to 20% of a finely disperse inorganic filler having a particle size below 500 nm.

16. In the molding of a polymerizable composition containing a polymerizable monomer and a microporous inorganic filler, the improvement which comprises employing as the filler one which has
(a) an average particle size of 0.5 to 50$\mu$;
(b) a BET surface area of at least 200 $m^2/g$;
(c) a pore volume of 0.7 to 5 ml/g, and
(d) a pore diameter of 10 to 50 nm.

17. The method according to claim 16, wherein the filler has
(a) an average particle size of 1 to 20$\mu$;
(b) a BET surface area of 300 to 600 $m^2/g$;
(c) a pore volume of 1 to 3 ml/g; and
(d) a pore diameter of about 20 nm;
the filler comprises silanized $SiO_2$, the polymerizable monomer comprises bis-GMA, and the composition by weight comprises 30 to 60% of the polymerizable monomer, 30 to 50% of the inorganic filler and up to 20% of a finely disperse inorganic filler having a particle size below 500 nm.

* * * * *